(12) United States Patent
Hallock et al.

(10) Patent No.: US 10,948,745 B2
(45) Date of Patent: Mar. 16, 2021

(54) VISION-PROTECTING FILTER LENS HAVING ORGANIC POLYMER MULTILAYER AND NEUTRAL-DENSITY OPTICAL FILTER

(71) Applicant: 3M INNOVATIVE PROPERTIES COMPANY, St. Paul, MN (US)

(72) Inventors: Michael E. Hallock, Hager City, WI (US); Joy L. Manske, Menomonie, WI (US); Britton G. Billingsley, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 852 days.

(21) Appl. No.: 15/532,902

(22) PCT Filed: Nov. 25, 2015

(86) PCT No.: PCT/US2015/062663
§ 371 (c)(1),
(2) Date: Jun. 2, 2017

(87) PCT Pub. No.: WO2016/089695
PCT Pub. Date: Jun. 9, 2016

(65) Prior Publication Data
US 2017/0363884 A1 Dec. 21, 2017

Related U.S. Application Data

(60) Provisional application No. 62/087,843, filed on Dec. 5, 2014.

(51) Int. Cl.
*G02C 7/10* (2006.01)
*A42B 3/22* (2006.01)
(Continued)

(52) U.S. Cl.
CPC ............... *G02C 7/10* (2013.01); *A42B 3/225* (2013.01); *A61F 9/022* (2013.01); *A61F 9/065* (2013.01);
(Continued)

(58) Field of Classification Search
CPC .......... A42B 3/225; A61F 9/022; A61F 9/065; A62B 7/10; A62B 9/04; A62B 18/082;
(Continued)

(56) References Cited

U.S. PATENT DOCUMENTS 3,290,203 A 12/1966 Antonson
3,946,442 A 3/1976 Wallander
(Continued)

FOREIGN PATENT DOCUMENTS

CN 103735353 4/2014
DE 3227366 1/1984
(Continued)

OTHER PUBLICATIONS

Extended European Search Report, EP15865168.7; dated Jun. 18, 2018; 4 pages.
(Continued)

*Primary Examiner* — Ryan S Dunning
(74) *Attorney, Agent, or Firm* — Kenneth B. Wood (57) ABSTRACT

A vision-protecting filter lens, including a multilayer optical film and a neutral-density optical filter.

25 Claims, 4 Drawing Sheets

(51) Int. Cl.
 *A61F 9/02* (2006.01)
 *A61F 9/06* (2006.01)
 *A62B 7/10* (2006.01)
 *A62B 18/08* (2006.01)
 *G02B 5/20* (2006.01)

(52) U.S. Cl.
 CPC .............. *A62B 7/10* (2013.01); *A62B 18/082* (2013.01); *G02B 5/205* (2013.01); *G02B 5/208* (2013.01); *G02C 7/104* (2013.01); *G02C 2202/16* (2013.01)

(58) Field of Classification Search
 CPC ........ G02B 5/205; G02B 5/206; G02B 5/208; G02B 5/223; G02B 5/23; G02B 5/26; G02B 5/281; G02B 5/282; G02B 5/283; G02B 5/285; G02B 5/286; G02B 5/287; G02B 5/288; G02C 7/10; G02C 7/102; G02C 7/104; G02C 7/107; G02C 7/108; G02C 2202/16
 USPC .................. 359/350–361, 580–590, 888
 See application file for complete search history.

(56) References Cited

U.S. PATENT DOCUMENTS

| | | | |
|---|---|---|---|
| 4,039,803 A | 8/1977 | Harsch | |
| 4,138,746 A | 2/1979 | Bergmann | |
| 4,215,436 A | 8/1980 | Ketterer | |
| 4,542,538 A | 9/1985 | Moretti | |
| 5,991,072 A | 11/1999 | Solyntjes | |
| 6,085,358 A | 7/2000 | Cogan | |
| 6,157,490 A | 12/2000 | Wheatley | |
| 6,352,761 B1 | 3/2002 | Hebrink | |
| 6,388,813 B1 | 5/2002 | Wilson | |
| 6,449,093 B2 | 9/2002 | Hebrink | |
| 6,463,590 B1 | 10/2002 | Dean | |
| 6,725,467 B2 | 4/2004 | Harding | |
| 6,777,055 B2 | 8/2004 | Janssen | |
| 6,783,349 B2 | 8/2004 | Neavin | |
| 7,005,176 B2 | 2/2006 | Tojo | |
| 7,184,217 B2 | 2/2007 | Wilson | |
| 7,264,873 B2 | 9/2007 | Katoh | |
| 8,015,970 B2 | 9/2011 | Klun | |
| 8,261,375 B1 | 9/2012 | Reaux | |
| 8,270,089 B2 | 9/2012 | Chiu | |
| 8,427,742 B2 | 4/2013 | Kim | |
| 8,441,724 B2 | 5/2013 | You | |
| 8,693,102 B2 | 4/2014 | Wilson | |
| 8,746,880 B2 | 6/2014 | Fukagawa | |
| 8,782,820 B2 | 7/2014 | Park | |
| 8,873,170 B2 | 10/2014 | Patil | |
| 2002/0066742 A1 | 6/2002 | Stubbs | |
| 2002/0159159 A1 | 10/2002 | Wilson | |
| 2004/0027706 A1 | 2/2004 | Nakajima | |
| 2004/0034608 A1 | 2/2004 | de Miranda | |
| 2005/0002108 A1 | 1/2005 | Wilson | |
| 2005/0186421 A1 | 8/2005 | Choi | |
| 2005/0243425 A1 | 11/2005 | Wheatley | |
| 2006/0084780 A1 | 4/2006 | Hebrink | |
| 2007/0264499 A1 | 11/2007 | Choi | |
| 2008/0026238 A1 | 1/2008 | Miyako | |
| 2008/0151147 A1 | 6/2008 | Weber et al. | |
| 2008/0151371 A1 | 6/2008 | Weber et al. | |
| 2009/0229044 A1 | 9/2009 | Gill | |
| 2009/0268157 A1* | 10/2009 | Krieg-Kowald | G02B 5/223 351/159.63 |
| 2009/0283133 A1 | 11/2009 | Hebrink | |
| 2009/0283144 A1 | 11/2009 | Hebrink | |
| 2011/0283443 A1 | 11/2011 | Simpson | |
| 2012/0287117 A1 | 11/2012 | Weber | |
| 2013/0135742 A1 | 5/2013 | Fukagawa | |
| 2013/0174312 A1* | 7/2013 | Chen | A61F 9/065 2/8.7 |
| 2013/0321915 A1 | 12/2013 | Chien | |
| 2014/0215673 A1 | 8/2014 | Lilenthal | |
| 2014/0220283 A1 | 8/2014 | Wilson | |
| 2015/0146161 A1* | 5/2015 | Rigato | G02B 5/282 351/159.6 |

FOREIGN PATENT DOCUMENTS

| | | |
|---|---|---|
| DE | 19949991 | 4/2001 |
| EP | 0678288 | 10/1995 |
| GB | 559865 | 3/1944 |
| GB | 2115685 | 9/1983 |
| GB | 2162960 | 2/1986 |
| GB | 2352961 | 2/2001 |
| GB | 2398725 | 9/2004 |
| JP | 07117065 | 5/1995 |
| JP | 2014-030908 | 2/2014 |
| KR | 2011-0052296 | 5/2011 |
| KR | 101345238 | 12/2013 |
| WO | WO 2002-32984 | 4/2002 |
| WO | WO 2003-060563 | 7/2003 |
| WO | WO 2007-083900 | 7/2007 |
| WO | WO 2008-018442 | 2/2008 |
| WO | WO 2008-074176 | 6/2008 |
| WO | WO 2008-114058 | 9/2008 |
| WO | WO 2009-140493 | 11/2009 |
| WO | WO 2010-001750 | 1/2010 |
| WO | WO 2012-133602 | 10/2010 |
| WO | WO 2013-178563 | 12/2013 |
| WO | WO 2014-052009 | 4/2014 |
| WO | WO 2015-002776 | 1/2015 |
| WO | WO 2015-134380 | 9/2015 |

OTHER PUBLICATIONS

3M Cool Mirror Film 330, Technical Data Sheet, May 2013, 2 pages.
3M Crystalline Automotive Window Films, 10 pages.
3M Sun Control Window Film, 2 pages.
3M Powered & Supplied Air Respirators, [Online Retrieved on Aug. 9, 2017], URL <http://solutions.3m.com/3MContentRetrievalAPI/BlobServlet?locale=en_WW&lmd=1309359316000&assetId=1258565658949&assetType=MMM_Image&blobAttribute=ImageFile> pp. 1.
Padiyath; "Spectrally Selective Window Films"; Society of Vacuum Coaters, 50th Annual Technical Conference Proceedings, 2007, pp. 186-190.
Satas, Handbook of Pressure-Sensitive Adhesive Technology, 172 (1989).
UVEX Lens Technology Brochure, 23 pages.
International Search Report for PCT International Application No. PCT/US2015/062663, dated Mar. 18, 2016, 3 pages.

* cited by examiner

VISION-PROTECTING FILTER LENS HAVING ORGANIC POLYMER MULTILAYER AND NEUTRAL-DENSITY OPTICAL FILTER

BACKGROUND

Many activities may benefit from vision protection due to the potential presence of undesirable levels of visible, ultraviolet, and/or infrared radiation. One example of such an activity is welding. Safety standards for industrial eye and face protection for welding and other activities are published by the American National Standards Institute, Inc. (ANSI) in ANSI Z87.1-2010, incorporated herein by reference. The ANSI standards define a set of shade numbers (ratings) based on the weighted transmittance of luminous, far ultraviolet, near ultraviolet, infrared, and blue light.

SUMMARY

In broad summary, herein is disclosed a vision-protecting filter lens, comprising a multilayer optical film and a neutral-density optical filter. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Figure 8:
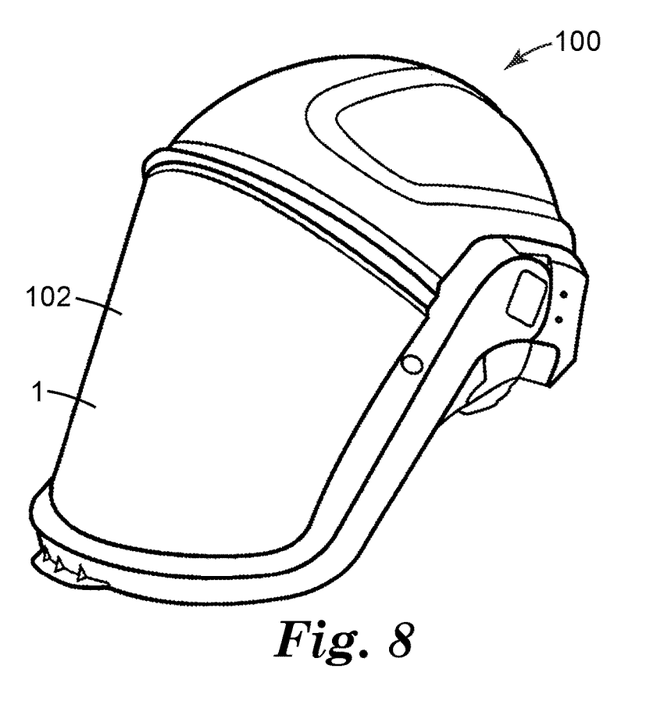
FIG. 8 depicts an exemplary personal-protection apparatus with which the herein-disclosed vision-protecting filter lens may be used.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "up" and "down", and "first" and "second" may be used in this disclosure, it should be understood that those terms are used in their relative sense only unless otherwise noted. Terms such as outward, outwardmost etc., refer to a direction that, when a personal-protection apparatus is fitted to a user, is toward a source of radiation from which the user's eyes are desired to be shielded. Thus, for example, FIG. 8 is a view of the outward side of a headgear. Terms such as inward, inwardmost, etc., refer to a direction that is generally away from the outward direction (i.e., a direction that is toward the user's eyes). All references herein to numerical parameters (dimensions, ratios, and so on) are understood to be calculable (unless otherwise noted) by the use of average values derived from a number of measurements of the parameter, particularly for the case of a parameter that is variable.

DETAILED DESCRIPTION

Glossary

By a filter lens is meant at least one multilayer optical film, and a neutral-density optical filter, that are non-separably joined together as a sheetlike assembly that can be handled as a single unit (e.g., that can be mounted onto a visible-light-transmissive pane of a personal-protection apparatus).

By a vision-protecting filter lens is meant a filter lens configured for use in a personal protection device that is worn by a user (e.g., a headgear such as a helmet or visor, eyewear such as e.g. goggles, and the like). By definition, vision-protecting filter lenses do not encompass automotive or architectural windows, electronic displays (such as of smartphones, tablet computers, televisions and monitors, etc.), and components thereof.

By a multilayer optical film is meant a film made of a plurality of coextruded, non-separable, alternating layers of a first, birefringent organic polymer and a second, other organic polymer, and which is designed to preferentially reflect radiation in a primary reflection band that extends over a predetermined wavelength range. (The term non-separable denotes components that are not separated from each other in ordinary use of an entity of which the components are parts).

By a neutral-density optical filter is meant a plurality of layers that collectively exhibit a percent transmission of less than 30 over the wavelength range of 300 nm to 1500 nm, and a visible-light-transmission slope with an absolute value of less than about 7 percent transmission per 100 nm.

By a Shade Number is meant a parameter measured and calculated according to ANSI Z87.1-2010.

By a left band edge is meant the wavelength at which the percent reflection exhibited by the left (shorter-wavelength) edge of a primary reflection band of a multilayer optical film, crosses 50.

Figure 1:
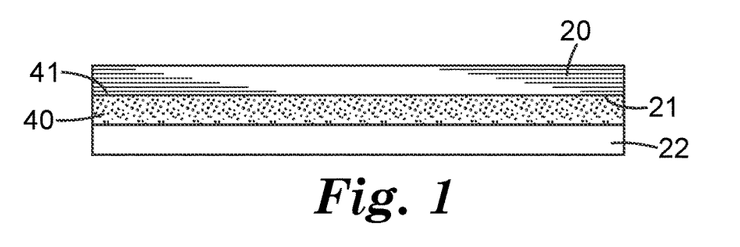
FIG. 1 is a side schematic cross-sectional view of an exemplary vision-protecting filter lens as disclosed herein.

Disclosed herein is a filter lens 1, the filter lens comprising at least one multilayer optical film 20 in combination with a neutral-density optical filter 40, as shown in exemplary embodiment in FIG. 1. Multilayer optical film 20 and neutral-density optical filter 40 are in the same optical path; often, a major surface (e.g., major surface 41 of FIG. 1) of a layer of neutral-density optical filter 40 will be bonded to a major surface (e.g., major surface 21 of FIG. 1) of multilayer optical film 20. (If an adhesive is used in such bonding, such an adhesive is considered to be a part of neutral-density filter 40 as discussed in detail later herein, thus in such a case a major surface of the adhesive may provide major surface 41 of neutral-density optical filter 40.) Filter lens 1 is configured to be used with a personal-protection apparatus 100 (e.g., a respirator), as shown in exemplary embodiment in FIG. 8. Filter lens 1 accordingly exhibits a Shade Number of at least 3, as discussed in detail later herein.

Figure 2:
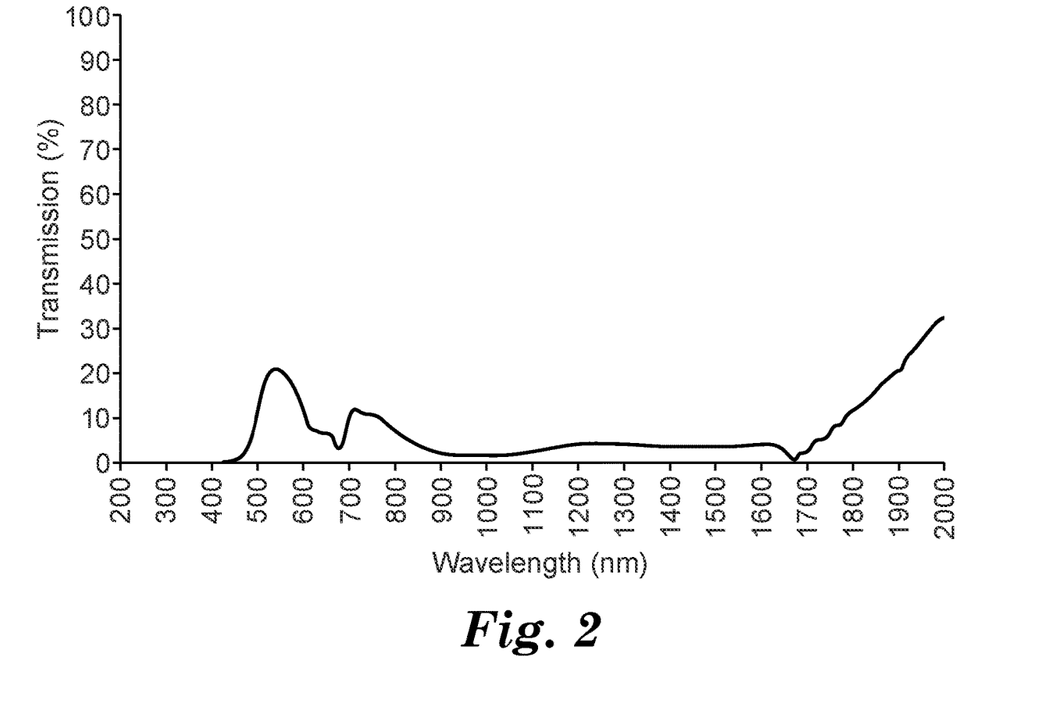
FIG. 2 contains transmission spectra for a vision-protecting filter lens of the prior art.

Filter lens 1 as disclosed herein addresses a long-standing issue with vision-protecting filters as used e.g. in personal-protection apparatus. This is illustrated in FIG. 2, which presents published data for percent transmission of radiation as a function of wavelength, for a commercially available vision-protecting lens with a Shade Number of 3 (specifically, for a UVEX INFRA-DURA 3.0 lens available from Sperian Protection Americas, Inc., Smithfield, IR). As can be seen from FIG. 2, the percent transmission allowed by this lens in the green-light range (approximately 500-570 nm nanometers (nm)), is significantly higher than the percent transmission allowed by this lens in the red-light range (approximately 620-740 nm). (All such wavelength ranges (e.g. green, red, IR, and near-IR) as mentioned herein are nominal ranges, since some differences exist in the boundaries between such ranges as reported by different sources.) Such a phenomenon can sometimes cause the visible light that passes through a vision-protecting lens to have a pronounced green color as viewed by the user of the lens. This may be perceived as undesirable by some users, and is a long standing issue with vision-protecting apparatus as used e.g. in welding operations (as remarked on e.g. by PCT Patent Application Publication WO 2008/074176). This phenomenon appears to result at least in part from the fact that, in order to meet the requirements of ANSI Z87.1-2010, the transmission of radiation in the infrared (IR) range must be significantly limited (e.g., to a (weighted) maximum infrared average transmittance of less than approximately 9 percent in the case of a product with a Shade Number of 3). While not wishing to be limited by theory or mechanism, the inventors have found that the use of conventional IR-blocking (e.g., IR-absorbing) materials to accomplish this (in particular, the use of such materials to block near-IR) can result in a significant reduction of transmitted red light (in addition to the desired reduction in IR), giving rise to the above-described phenomenon.

The inventors have discovered that a novel and unique combination of optical elements can minimize the above problem. Specifically, filter lens 1 as used herein relies on a neutral-density filter 40 that exhibits a percent transmission of less than 30 over the wavelength range of 300 nm to 1500 nm (thus covering from the ultraviolet (UV) range into the IR range) and in particular exhibits a relatively flat percent transmission over the visible light range, as discussed later herein in detail. The experimentally obtained percent transmission over the range of 300-2500 nm is presented in FIG. 3, and a magnified view of the percent transmission over the range of 400-1000 nm is presented in FIG. 4, for an exemplary neutral-density filter.

Neutral-density filter 40 is used in combination with at least one multilayer optical film (MOF) 20, which multilayer optical film preferentially reflect radiations in a primary reflection band that at least includes a significant portion of the near-IR range (approximately 740-1400 nm). The experimentally obtained percent reflection over the range of 400-2000 nm is presented in FIG. 5 for an exemplary multilayer optical film.

The inventors have discovered that combining a neutral-density filter 40 with at least one appropriately configured multilayer optical film 20 can significantly reduce the transmission of near-IR radiation, while transmitting an appropriate amount of light across the visible range (e.g., without unduly removing red light from the visible-light range). This is demonstrated in FIG. 7, which shows the result of combining an exemplary multilayer optical film (with a reflection spectra of the type presented in FIG. 6) with an exemplary neutral-density filter (with a transmission spectra of the type presented in FIGS. 3 and 4). It will be evident from FIG. 7 that the percent transmission in the near-IR range is reduced to a very low level, while allowing a percent transmission that is relatively high, and relatively flat, across much of the visible spectrum.

Arrangements as presented herein can thus achieve e.g. a Shade Number of 3, 4, 5, 6, or 7, while advantageously minimizing any tendency for the transmitted visible light to be biased toward green. These arrangements can be enhanced by positioning the left band edge ($BE_L$) of the primary reflection band of the multilayer optical film at or near the boundary between the red and infrared ranges, and also, if desired, by enhancing the sharpness (steepness) of the left band edge as discussed later. It is noted that even a multilayer optical film with the characteristics shown in FIG. 6 (i.e., with a left band edge ($BE_L$) located at approximately 650 nm) was found to not unduly reduce transmission of red light. That is, even though a multilayer optical film with a left band edge falling at approximately 650 nm might be expected to disadvantageously reduce the percent transmission in the red-light range, filter lenses using such a multilayer optical film were demonstrated to exhibit excellent red-green balance of transmitted light as characterized quantitatively by measurement of CIE a* parameters, and also as characterized by qualitative evaluation by human subjects. (Such filter lenses were also able to meet the ANSI Z87.1-2010 requirements (in particular, those for a Shade Number of 3)). In additional investigations, a multilayer optical film of the type characterized in FIG. 5 (with a left band edge at approximately 860 nm) could also be used to form acceptable filter lenses. It is thus apparent that a multilayer optical film with a left band edge falling in the range of e.g. 600-900 nm can serve in a vision-protecting filter lens as disclosed herein. In various embodiments a multilayer optical film 20 as used in filter lens 1, will exhibit a left band edge located at a wavelength of at least about 600, 650, 700, or 750 nm. In further embodiments, multilayer optical film 20 will exhibit a left band edge located at a wavelength of at most about 900, 850, 750, or 700 nm. (It is emphasized, however, that a multilayer optical film configured in this manner may not necessarily achieve the results described herein, unless used in concert with a neutral-density filter configured as described herein.)

Figure 5:
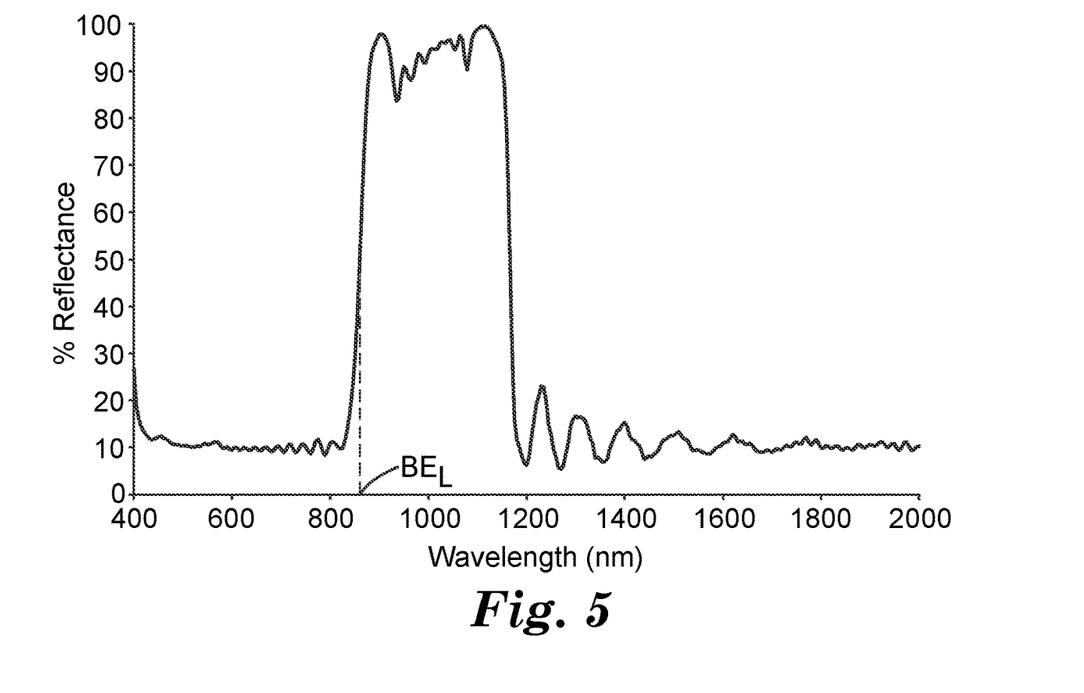
FIG. 5 contains reflection spectra for an exemplary multilayer optical film as disclosed herein.
Figure 6:
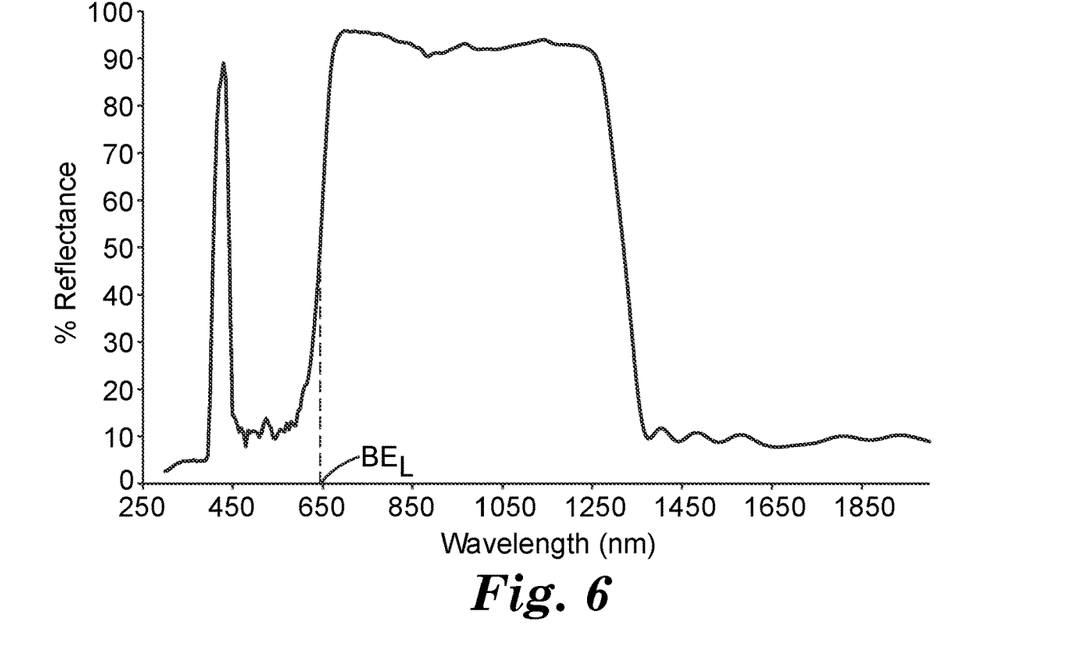
FIG. 6 contains reflection spectra for another exemplary multilayer optical film as disclosed herein.
Figure 7:
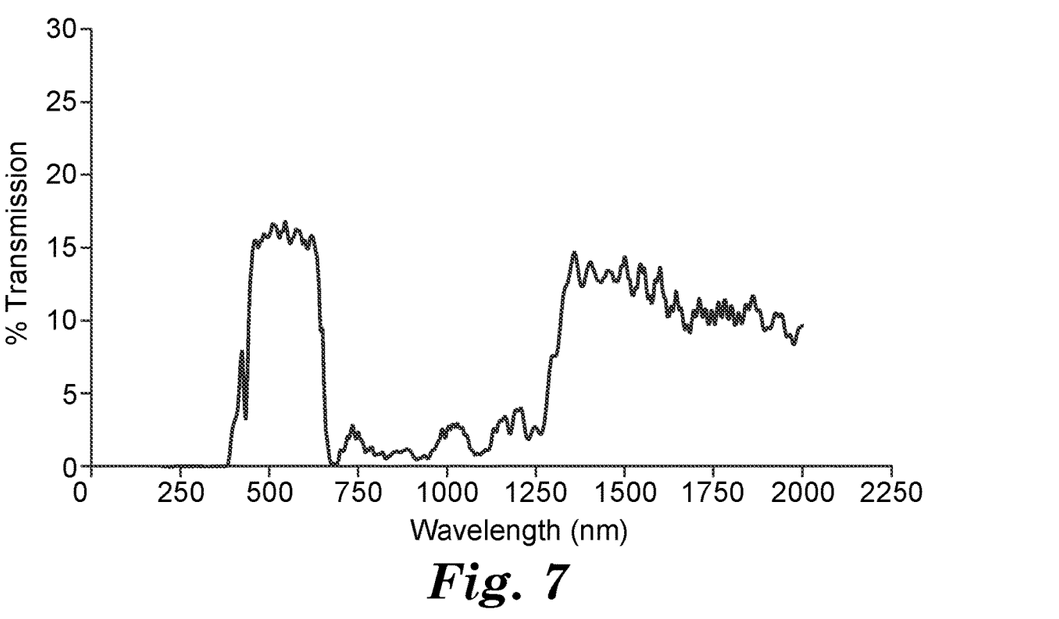
FIG. 7 contains transmission spectra for an exemplary vision-protecting filter lens comprising an exemplary neutral-density optical filter in combination with an exemplary multilayer optical film.

The left band edge of a primary reflection band is defined herein at the wavelength (on the left, shorter-wavelength side of the primary reflection band) at which the reflection crosses the 50 percent value. (The left band edges $BE_L$ are denoted on FIGS. 5 and 6). It is noted in passing that the ordinary artisan will understand the concept of a primary (first-order) reflection band, and higher-order reflection bands, of a multilayer optical film (in FIG. 6, a higher-order reflection band is evident at about 440 nm). The slope of a left band edge can be conveniently calculated by determining the wavelengths that correspond to 70 percent transmission and 30 percent transmission (with the interval thus being centered on 50 percent transmission), and taking the ratio of the percent transmission increment to the wavelength increment (using 30 percent transmission, and the corresponding wavelength, as the reference point). By way of specific example, the slope of the left band edge of FIG. 6 is approximately (70−30)/(657−628), or approximately 1.4 percent transmission per nm. In various embodiments, the left band edge slope exhibited by a multilayer optical film 20 of filter lens 1 may be at least about 1.0, 1.4, 2.0, 4.0, or 8.0. In further embodiments, the left band edge slope may be at most about 40, 20, or 10 percent transmission per nm. Methods of increasing (steepening) the slope of a band edge are disclosed e.g. in U.S. Pat. No. 6,157,490, which is incorporated by reference herein in its entirety for this purpose.

Neutral-density filter 40 by definition exhibits a percent transmission of less than 30 over the wavelength range of 300 nm to 1500 nm. By this is meant that there is no wavelength anywhere in that range at which filter 40 exhibits a percent transmission of 30 or greater. In further embodiments, neutral-density filter 40 may (as in the exemplary neutral-density filter characterized in FIG. 3) exhibit a percent transmission of less than 30, over the range from 200 nm to 2500 nm. In still further embodiments, neutral-density filter 40 exhibits a percent transmission, over the wavelength range of 300 nm to 1500 nm, of less than about 25, 20, 15, or 10. In specific embodiments, neutral-density filter 40 exhibits an average percent transmission (averaged over the range of 300-1500 nm), or less than about 30, 25, 20, 15, or 10.

Figure 4:
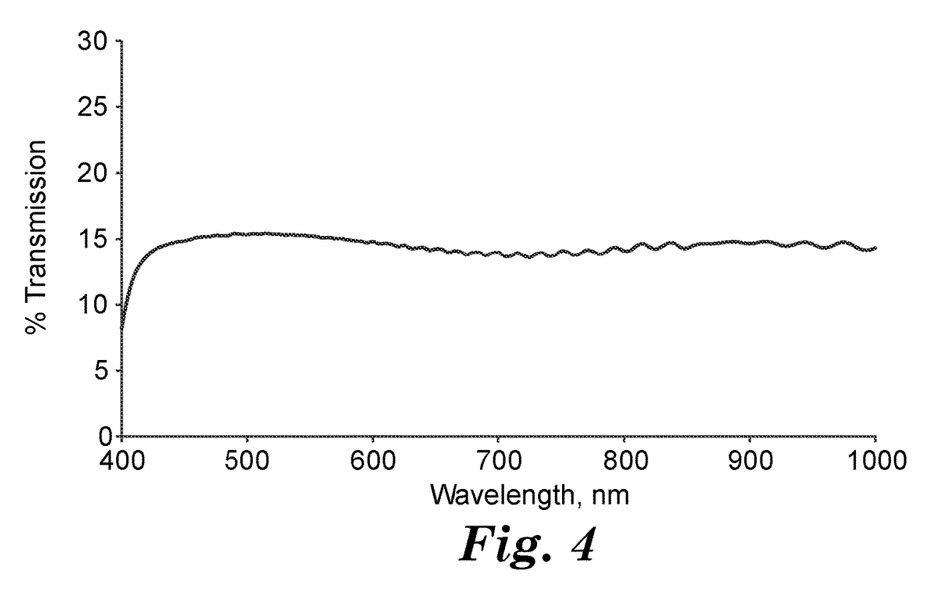
FIG. 4 contains a magnified view of the visible-range portion of the transmission spectra of the neutral-density optical filter of FIG. 3.

Also as noted, by definition neutral-density filter 40 exhibits a visible-light-transmission slope that has an absolute value of less than about 7 percent transmission per 100 nm. A visible-light-transmission slope may be conveniently calculated by noting the percent transmission at 500 nm and 700 nm, and taking the ratio of the percent transmission increment to the wavelength increment (using 30 percent transmission, and the corresponding wavelength, as a basis). By way of specific example, the visible-light-transmission slope of FIG. 4 is approximately (14.0−15.3)/(700−500), or minus 0.65 percent transmission per 100 nm. The absolute value of the slope may be used for convenience. In various embodiments, the absolute value of the visible-light-transmission slope of a neutral-density filter may be at most about 6, 4, 2, 1.0, or 0.50, percent transmission per 100 nm.

As noted in the Glossary, by a multilayer optical film is meant a plurality of coextruded, alternating layers of a first, birefringent organic polymer and a second, other organic polymer, the layers being designed to collectively reflect radiation in a primary reflection band that extends over a predetermined wavelength range. The ordinary artisan will understand that many such optical films operate as quarter-wave stacks, in which constructive and destructive interference from the alternating, optically active layers collectively provide a reflection spectrum. The thickness of the individual layers, the total number of layers, the refractive indices of the layers, and so on, may be chosen in combination to provide a predetermined reflection spectrum, as is well known.

One or more multilayer optical films 20, each having alternating layers of at least one birefringent polymer and one second polymer, may be employed in creating filter lens 1. Materials suitable for making the at least one birefringent layer of the multilayer optical film include organic polymers (e.g., polyesters, copolyesters, and modified copolyesters). In this context, the term "polymer" will be understood to include homopolymers and copolymers, as well as polymers or copolymers that may be formed in a miscible blend, for example, by co-extrusion or by reaction, including transesterification. The terms "polymer" and "copolymer" include both random and block copolymers. Polyesters suitable for use in some exemplary multilayer optical films constructed according to the present disclosure generally include carboxylate and glycol subunits and can be generated by reactions of carboxylate monomer molecules with glycol monomer molecules. Each carboxylate monomer molecule has two or more carboxylic acid or ester functional groups and each glycol monomer molecule has two or more hydroxy functional groups. The carboxylate monomer molecules may all be the same or there may be two or more different types of molecules. The same applies to the glycol monomer molecules. Also included within the term "polyester" are polycarbonates derived from the reaction of glycol monomer molecules with esters of carbonic acid.

Suitable carboxylate monomer molecules for use in forming the carboxylate subunits of the polyester layers include, for example, 2,6-naphthalene dicarboxylic acid and isomers thereof; terephthalic acid; isophthalic acid; phthalic acid; azelaic acid; adipic acid; sebacic acid; norbornene dicarboxylic acid; bi-cyclo-octane dicarboxylic acid; 1,4-cyclohexane dicarboxylic acid and isomers thereof; t-butyl isophthalic acid, trimellitic acid, sodium sulfonated isophthalic acid; 4,4'-biphenyl dicarboxylic acid and isomers thereof; and lower alkyl esters of these acids, such as methyl or ethyl esters. The term "lower alkyl" refers, in this context, to C1-C10 straight-chained or branched alkyl groups.

Suitable glycol monomer molecules for use in forming glycol subunits of the polyester layers include ethylene glycol; propylene glycol; 1,4-butanediol and isomers thereof; 1,6-hexanediol; neopentyl glycol; polyethylene glycol; diethylene glycol; tricyclodecanediol; 1,4-cyclohexanedimethanol and isomers thereof; norbornanediol; bicyclo-octanediol; trimethylol propane; pentaerythritol; 1,4-benzenedimethanol and isomers thereof; bisphenol A; 1,8-dihydroxy biphenyl and isomers thereof; and 1,3-bis (2-hydroxyethoxy)benzene.

An exemplary polymer useful as the birefringent layer in the multilayer optical films of the present invention is polyethylene naphthalate (PEN), which can be made, for example, by reaction of naphthalene dicarboxylic acid with ethylene glycol. Polyethylene 2,6-naphthalate (PEN) is frequently chosen as a birefringent polymer. PEN has a large positive stress optical coefficient, retains birefringence effectively after stretching, and has little or no absorbance within the visible range. PEN also has a large index of refraction in the isotropic state. Its refractive index for polarized incident light of 550 nm wavelength increases when the plane of polarization is parallel to the stretch direction from about 1.64 to as high as about 1.9. Increasing molecular orientation increases the birefringence of PEN. The molecular orientation may be increased by stretching the material to greater stretch ratios and holding other stretching conditions fixed. Copolymers of PEN (CoPEN), such as those described in U.S. Pat. Nos. 6,352,761 and 6,449,093 are particularly useful for their low temperature processing capability making them more coextrusion compatible with less thermally stable second polymers. Other semicrystalline polyesters suitable as birefringent polymers include, for example, polybutylene 2,6-naphthalate (PBN), polyethylene terephthalate (PET), and copolymers thereof such as those described in U.S. Pat. No. 6,449,093 and U.S. Patent Application Publication 20060084780. Alternatively, syndiotactic polystyrene (sPS) is another useful birefringent polymer.

The second polymer of the multilayer optical film can be made from a variety of polymers e.g. having glass transition temperatures compatible with that of the first birefringent polymer and having a refractive index similar to the isotropic refractive index of the birefringent polymer. Examples of other polymers suitable for use in optical films and, particularly, in the second polymer include vinyl polymers and copolymers made from monomers such as vinyl naphthalenes, styrene, maleic anhydride, acrylates, and methacrylates. Examples of such polymers include polyacrylates, polymethacrylates, such as poly (methyl methacrylate) (PMMA), and isotactic or syndiotactic polystyrene. Other polymers include condensation polymers such as polysulfones, polyamides, polyurethanes, polyamic acids, and polyimides. In addition, the second polymer can be formed from homopolymers and copolymers of polyesters, polycarbonates, fluoropolymers, and polydimethylsiloxanes, and blends thereof.

Other exemplary suitable polymers, especially for use as the second polymer, include homopolymers of polymethylmethacrylate (PMMA), such as those available from Ineos Acrylics, Inc., Wilmington, Del., under the trade designations CP71 and CP80, or polyethyl methacrylate (PEMA), which has a lower glass transition temperature than PMMA. Additional second polymers include copolymers of PMMA (coPMMA), such as a coPMMA made from 75 wt % methylmethacrylate (MMA) monomers and 25 wt % ethyl acrylate (EA) monomers, (available from Ineos Acrylics, Inc., under the trade designation Perspex CP63), a coPMMA formed with MMA comonomer units and n-butyl methacrylate (nBMA) comonomer units, or a blend of PMMA and poly(vinylidene fluoride) (PVDF).

Yet other suitable polymers, especially useful as the second polymer, include polyolefin copolymers such as poly (ethylene-co-octene) (PE-PO) available from Dupont Performance Elastomers under the trade designation Engage 8200, poly (propylene-co-ethylene) (PPPE) available from Fina Oil and Chemical Co., Dallas, Tex., under the trade designation Z9470, and a copolymer of atactic polypropylene (aPP) and isotactic polypropylene (iPP). The multilayer optical films can also include, for example in the second polymer layers, a functionalized polyolefin, such as linear low density polyethylene-g-maleic anhydride (LLDPE-g-MA) such as that available from E.I. duPont de Nemours & Co., Inc., Wilmington, Del., under the trade designation Bynel 4105.

Preferred polymer compositions suitable as the second polymer in alternating layers with the at least one birefringent polymer include PMMA, CoPMMA, polydimethyl siloxane oxamide based segmented copolymer (SPOX), fluoropolymers including homopolymers such as PVDF and copolymers such as those derived from tetrafluoroethylene, hexafluoropropylene, and vinylidene fluoride (THV), blends of PVDF/PMMA, acrylate copolymers, styrene, styrene copolymers, silicone copolymers, polycarbonate, polycarbonate copolymers, polycarbonate blends, blends of polycarbonate and styrene maleic anhydride, and cyclic-olefin copolymers. Preferred combinations of birefringent layers and second polymer layers may include, for example, the following: PET/THV, PET/SPOX, PEN/THV, PEN/SPOX, PEN/PMMA, PET/CoPMMA, PEN/CoPMMA, CoPEN/PMMA, CoPEN/SPOX, sPS/SPOX, sPS/THV, CoPEN/THV, PET/fluoroelastomers, sPS/fluoroelastomers and CoPEN/fluoroelastomers.

In general, the selection of the polymer compositions used in creating the multilayer optical film can be made in view of the desired properties (e.g., centerpoint, width, left band edge, and left band edge sharpness) of the primary reflection band. Higher refractive index differences between the birefringent polymer and the second polymer create more optical power thus enabling more reflective bandwidth. Alternatively, additional layers may be employed to provide more optical power.

A multilayer optical film may be produced e.g. according to processing techniques such as those described in U.S. Pat. No. 6,783,349. Beyond the choices of first and second polymer compositions, the methods of producing a multilayer optical film may be chosen as desired to provide a controlled spectrum. For example, if desired the layer thickness values can be controlled so that first (thinnest) optical layers of the film have a quarter-wave optical thickness (index times physical thickness) corresponding approximately to the desired left band edge, progressing to the thickest layers which can have a quarter-wave optical thickness corresponding approximately to the desired right band edge. If desired, the profile between these two endpoints may be approximately linear.

Convenient techniques for providing a multilayer optical film with a predetermined primary reflection band by way of control of layer thickness profile, include adjusting axial rod zone power settings based on the difference of the target layer thickness profile and the measured layer profile. The axial rod power increase needed to adjust the layer thickness values in a given feedblock zone may first be calibrated in terms of watts of heat input per nanometer of resulting thickness change of the layers generated in that heater zone, as discussed in U.S. Pat. No. 6,783,349.

In some embodiments, two or more multilayer optical films (whether similar or identical to each other, or differing significantly) may be used in the filter lens 1. In some embodiments, the two or more multilayer optical films may be laminated together (e.g., via a pressure sensitive adhesive) to form a single module that is then mated to the desired neutral-density filter. In alternative embodiments, the two or more multilayer optical films may be brought together with layers of the neutral-density filter separately (the resulting filter lens 1 thus might comprise at least one or more layers of the neutral-density filter interspersed between two multilayer optical films). A multilayer optical film, as made, may have a protective boundary layer (such as for example those disclosed in the U.S. Pat. No. 6,783,349) attached to one or both major surfaces thereof. Such a protective boundary layer is often not optically active (that is, it does not have any significant effect on the properties of the primary reflection band); thus, strictly speaking, such a protective boundary layer (even though supplied to filter lens 1 along with the multilayer optical film) becomes part of the neutral-density filter 40, since a multilayer optical film as defined herein only includes the actual optically active alternating layers of the multilayer optical film.

Multilayer optical films are described in further detail in U.S. Patent Application Publication 20090283144, in U.S. Provisional Patent Application Ser. No. 61/841,565, and in U.S. Provisional Patent Application Ser. No. 61/947,238, all of which are incorporated by reference in their entirety herein.

As noted in the Glossary, by a neutral-density optical filter is meant a plurality of layers (i.e., at least two layers) that collectively exhibit a percent transmission of less than 20 over the wavelength range of 300 nm to 1500 nm, and a visible-light-transmission slope with an absolute value of less than about 7 percent transmission per 100 nm. By definition, a neutral-density optical filter will exhibit a nominal luminous transmittance of at least 0.10 (as calculated according to ANSI Z87.1-2010), thus corresponding to a Shade Number of 8 or lower. Moreover, a neutral-density optical filter must allow an image to be transmitted therethrough with sufficient clarity to meet the resolving power requirements of ANSI Z87.1-2010. It will thus be appreciated a neutral-density optical filter as defined herein will not encompass e.g. an opaque layer or set of layers, nor a layer or set of layers that are sufficiently translucent or hazy that an image cannot be perceived therethrough (e.g. an optical diffuser, and the like).

A neutral-density-optical filter can be provided by any suitable layers, of any suitable composition, as long as the layers collectively exhibit the above-described transmission of radiation. The layers can each operate by any suitable mechanism or combination thereof, e.g. by absorbtion, reflection, scattering, and so on; different layers may of course operate by the same mechanism(s), or by different mechanisms or combinations of mechanisms. The individual layers can each be comprised of any suitable material and each layer can include any desired additive or additives, in any combination. The layers do not have to be organic polymeric materials but rather can include, or consist of, e.g. inorganic materials (e.g., fillers, opacifiers, pigments, and so on), metals or metal oxides and so on. Dyes, UV blockers, IR blockers, and so on, may also be used. Various categories of components, their general attributes, and examples of materials falling into those categories, are discussed below. However, the categories presented herein, and descriptions of materials therein, are non-limiting characterizations that are used for convenience of description. The ordinary artisan will readily understand that some materials may serve more than one function (e.g., might absorb some radiation as well as reflecting some radiation) and may thus fall into more than one of the herein-disclosed categories.

In some embodiments, at least one layer of the neutral-density filter is an organic polymer layer. Such a layer may inherently perform a radiation-filtering function (e.g., it might, by virtue of its chemical structure, absorb at least some amount of UV). For example, certain polyethylene terephthalates are known to absorb UV radiation starting at around 360 nm, increasing markedly below 320, and in a very strong manner below 300 nm. Instead of, or in addition to the polymer itself performing a radiation-filtering function, the polymer may have one or more additives added thereto that performs a radiation-filtering function as discussed below. In some embodiments, an organic polymer layer may function, purely or in part, as a support layer (e.g., a layer upon which an at least semi-reflective metal or metal oxide layer is deposited, to which another film or films is laminated, and so on). An organic polymer layer may of course serve in any combination of the above roles. Whatever its function, an organic polymer layer may be comprised of any suitable material. Materials that are potentially suitable for use as an organic polymer layer of a neutral-density filter include acrylic polymers, such as acrylate, methacrylate, and copolymers thereof; polyethylene and copolymers thereof; polypropylene and copolymers thereof; polyvinylchloride and copolymers thereof; nylon; polycarbonate; and polyesters, such as polyethylene terephthalate, as well as other polymers known to those skilled in the art.

In some embodiments, at least one layer of the neutral-density filter comprises one or more inorganic materials. Such materials can include any desired pigment, filler, or the like. Such a material may provide blocking across a large segment of the radiation spectrum; or, such a material may block a targeted wavelength range. Two or more such materials, e.g. materials that each blocks a specific wavelength range, may be used in combination in pursuit of a neutral-density filter. A non-limiting list of potentially suitable materials includes calcium carbonate, barium sulfate, titanium dioxide, calcium carbonate, carbon black (which, for purposes herein, will be classified as an inorganic material), talc, silica, mica, kaolin and other clays, and so on. Such a material may be present as a layer (e.g., as a coating); or, such a material may be present within a layer. For example, one or more materials may be dispersed, e.g. compounded, into an organic polymer layer. (Many such materials are often compounded into organic polymers e.g. as melt additives, and are often referred to as pigments, fillers, and the like.) Intermediate constructions that loosely fall between, or into both, of these general categories also exist (e.g., a layer may comprise carbon black particles held together by a binder).

In some embodiments, at least one layer of the neutral-density filter comprises one or more metals, metal oxides, or combinations thereof. The terms metal and metal oxide are broadly used to encompass multi-metal compositions, e.g. alloys, mixtures, solid solutions, and so on, as well as single-composition layers). A non-limiting list of such materials includes silver, aluminum, gold, nickel, copper, titanium, indium tin oxide, antimony tin oxide, iron oxide, titanium dioxide, cerium oxide, zirconia, tantalum oxide, silicon dioxide, zinc oxide, aluminum oxide, niobia, and hafnia. Such materials may be, for example, present as a coating and/or as an additive e.g. in an organic polymer layer; moreover, such materials may perform reflection, scattering, and/or absorption of radiation. Often, such materials may perform more than one of these functions.

In some embodiments, one or more such materials may be vapor deposited (e.g., by physical vapor deposition (e.g. sputtering), by chemical vapor deposition, and so on), e.g. onto a supporting organic polymer layer. Such a material may be deposited at any desired thickness, and in various embodiments the deposited material might be present e.g. as discrete islands, or as a continuous coating of a desired average thickness. In some embodiments, a metal or metal oxide layer may be deposited e.g. by sol-gel methods and the like.

Any such layer or layers (e.g., one, two, three, four, or more layers) may be used, with e.g. the thickness of the metal or metal oxide layer, the number of layers, and so on, being chosen in combination with the properties of the materials, to provide the desired optical performance. If multiple layers are used, the metal and/or metal oxides in each layer may be the same, or may be different.

In some embodiments, at least one layer of the neutral-density filter comprises one or more dyes. The term dye is used to broadly encompass any molecular species that absorbs radiation and that is present (e.g., compounded into) in a carrier material such as e.g. an organic polymer, as a solution or as a liquid. The dividing line between dyes and pigments is often considered to be that pigments are at least semi-solid materials that e.g. dispersed (rather than being dissolved) in a carrier material. It is however emphasized that there may be no bright-line difference between dyes and pigments and the classifications herein are purely for convenience of description. Any suitable dye may be used. A non-limiting list of potentially suitable dyes includes those chosen from the broad groups including e.g. azo dyes, anthraquinone dyes, phthalocyanine dyes, thiazine dyes, indophenol dyes, and so on. Such dyes may be synthetic, or may be natural products (albeit purified, for example). Of course, a layer (e.g. an organic polymer layer) may include both one or more dyes and one or more pigments.

In some embodiments, at least one layer of the neutral-density filter comprises one or more ultraviolet (UV) blockers. This term is used to broadly signify materials that preferentially block (i.e., absorb) ultraviolet radiation. It will be appreciated of course that some UV blockers may be generally considered to be dyes or pigments (and vice versa). That is, specific UV absorbers are described in this section for completeness of disclosure; this does not imply that any material that is listed in some other section of this document, cannot perform at least some blocking, e.g. absorbtion, of UV. A non-limiting list of materials that may be suitable for use as a UV blocker includes hindered-amine light stabilizers (HALS), benzotriazoles, benzophenones, oxanilides, benzoxazinones, and like materials (such materials are often referred to as UV absorbers or UV stabilizers).

In some embodiments, at least one layer of the neutral-density filter comprises one or more infrared (IR) blockers. This term is used to broadly signify materials that preferentially block (i.e., absorb) infrared radiation. (In like manner to the discussion above regarding UV blockers, it will be appreciated that many materials specifically described in this section may fall into other sections herein, and vice versa.) A non-limiting list of materials that may be suitable for use as an IR blocker includes tin, antimony, indium, tin oxide, antimony oxide, indium oxide, indium-doped tin oxide, and mixtures thereof. In some embodiments at least one IR blocker and at least one UV blocker may be used in combination (whether in the same layer, or in different layers) in a neutral-density filter.

In some embodiments, a neutral-density filter may comprise (in addition to any of the above-described layers) any other layer or layers, for any desired purpose (whether or not such a layer provides any additional radiation-filtering function). For example, if a pressure-sensitive adhesive (PSA) is used to attach a neutral-density filter to a multilayer optical film to form vision-protecting filter lens 1, the PSA is by definition a part of the neutral-density filter (rather than a part of the multilayer optical film). This distinction is made in order to emphasize that a multilayer optical film as disclosed herein only includes the optically active alternating layers of the multilayer optical film; all other layers are considered to be a part of the neutral-density filter. It is emphasized that any such layer of the neutral-density filter may, or may not, provide any radiation-filtering function. For example, a PSA by which vision-protecting filter lens 1 is attached to a pane of a personal-protection apparatus, is a part of the neutral-density filter, even if the PSA is e.g. an optically clear PSA that performs little or no radiation-filtering.

However, it is also emphasized that in some embodiments, any layer (e.g., a binder, PSA, hardcoat, tie layer, and so on) of the neutral-density filter can provide at least some radiation filtering e.g. in addition to performing some other function. For example, an adhesive or binder that bonds two layers of the neutral-density filter to each other, that bonds a layer of the neutral-density filter to the multilayer optical film, or that bonds the filter lens to a pane of a person-protection apparatus, may comprise e.g. a UV blocker. (A binder comprising a UV blocker is described in U.S. Pat. No. 5,991,072). It will thus be appreciated that in particular embodiments, an adhesive (e.g., a PSA) that enables filter lens 1 to be attached to a pane of a personal protective apparatus, may comprise radiation-filtering properties that enable filter lens 1, in place on the pane, to meet the optical requirements of ANSI Z87.1-2010).

Depending on the particular construction, a neutral-density filter may include more than one (e.g. two, three, four or more) pressure-sensitive adhesive layers. The term pressure-sensitive adhesive will be understood by the ordinary artisan to mean an adhesive that meets the well-known Dahlquist criterion described in the Handbook of Pressure-Sensitive Adhesive Technology, D. Satas, $2^{nd}$ ed., page 172 (1989). This criterion defines a pressure-sensitive adhesive as one having a one-second creep compliance of greater than $1\times10^{-6}$ cm$^2$/dyne at its use temperature (for example, at temperatures in a range of from 15° C. to 35° C.). A neutral-density filter may of course include a removable release liner e.g. on a PSA that is to be used to attach filter lens 1 to a pane of a personal protective apparatus; such a liner will typically be removed prior to the use of filter lens 1.

Other layers of neutral-density filter may include at least one protective layer, e.g. that is provided on what will be the outward face of vision-protecting filter lens 1 when in use. By protective layer is meant any layer that protects some other layer from mechanical damage and/or from chemical attack (e.g., oxidation). In particular embodiments, such a protective layer may take the form of a hardcoat (which term will be well understood by the ordinary artisan). A non-limiting list of potentially suitable hardcoats includes acrylic hardcoats, silica-based hardcoats, siloxane hardcoats, melamine hardcoats, and the like. In some embodiments a hardcoat may serve a purely protective function (e.g. contributing little or no radiation filtering); in other embodiments, any such hardcoat may include any desired component(s) that provide a radiation-filtering property (including e.g. any of the above-mentioned polymers, organic materials, or inorganic materials).

In some embodiments, neutral-density filter 40 may include at least one protective layer whose purpose, at least in part, is to protect another layer (e.g., a metal layer) of neutral-density filter 40 from corrosion. Such a corrosion-protection layer may be e.g. an organic polymer layer, a sacrificial material (sacrificial anode) such as copper, or a relatively inert metal alloy such as an iron-nickel (e.g. Inconel) alloy.

As noted previously, in some embodiments a multilayer optical film may be made with a boundary layer on an outer face of the multilayer optical film. Such an outer boundary layer might be used e.g. as a protective layer, or as a compatibilizing (e.g., tie) layer for attachment of another layer thereto. For the purposes herein, such a boundary layer, if not significantly affecting the performance of the optical stack of alternating layers of the multilayer optical film, will be considered to be a part of neutral-density filter 40 (even if e.g. made by coextrusion with the alternating layers of the multilayer optical film).

The above descriptions are provided in order to illustrate the breadth of materials that may be used in providing a neutral-density filter. The characterization of a material is not meant to limit it to one particular category. It will be further appreciated that there may not always be a bright-line demarcation between materials of various categories. Furthermore, the existence of one particular descriptive section does not mean that a material that is mentioned in some other section, cannot perform the function described in that particular description section. For example, if a material is mentioned in some section of this document, but is not specifically mentioned in the section describing UV blockers, this does not imply that the material does not or cannot perform at least some blocking of UV. Thus in summary, the above characterizations are not meant to be limiting in any way. Furthermore, it is emphasized that any general category of material, and/or specific material, that is mentioned herein, may be used in combination with any other general category and/or specific material listed herein, as desired.

The providing of a neutral-density filter 40 along with at least one multilayer optical film 20 to provide a vision-protecting filter lens 1 may be achieved in any suitable manner. In some embodiments, neutral-density filter 40 may be provided as a module. By module is meant a single film (although such a film may of course have multiple layers, as achieved by lamination or any other suitable method) that is handleable as a unit and in which, by definition, no layers of the single film have a multilayer optical film interspersed therebetween. Such a module can be e.g. adhesively attached to a multilayer optical film to form filter lens 1. Such an approach may provide a filter lens 1 of the general type shown in FIG. 1. FIG. 1 includes an optional PSA 22 that can be used to e.g. attach filter lens 1 to a pane of a personal-protection apparatus; such a PSA, if present is considered to be part of neutral-density filter 40. (Moreover, any PSA that is used to bond neutral-density filter 40 to multilayer optical film 20 will also be considered to be part of neutral-density filter 40.)

However, in other embodiments, a neutral-density filter 40 need not ever have existed in the form of an above-described module. Rather, in the finished filter lens 1, neutral-density filter 40 may be collectively supplied by two or more layers that were never in the form of a single module. In other words, one or more layers provided on one major side of multilayer optical film 20, and one or more layers provided on the other major side of multilayer optical film 20, can act in combination to provide neutral-density filter 40. By way of a specific example, an organic polymer film comprising an organic dye or pigment might be attached to one major side of a multilayer optical film 20, and a metal or metal oxide vapor coating might be deposited on the other major side of the multilayer optical film 20. The polymer film and the metal or metal oxide coating (along with e.g. a PSA used to attach the film to the multilayer optical film) can thus provide a neutral-density filter even though these layers are not, and never were, in the form of a module as defined herein. It will be appreciated that numerous possible variations of this exist; all such variations are encompassed by the herein-disclosed concept of a neutral-density filter 40. In other words, a neutral-density filter may only exist in "latent" form until such time as vision-protecting filter lens 1 is actually assembled, at which time the various layers provide neutral-density filter 40 in combination.

In some embodiments, a multilayer optical film may be available in the form of a multilayer optical film product that comprises (e.g., as supplied by the manufacturer) at least one ancillary layer in addition to the optically active alternating layers of the multilayer optical film. (Such an ancillary layer may comprise any of the previously-discussed materials, e.g. one or more of metal or metal oxides, pigments, dyes, UV or IR blockers, and so on.) One or more additional layers can then be added to the multilayer optical film product (whether any such additional layer is in the form of a pre-existing layer that is e.g. laminated to the multilayer optical film product, is in the form of a surface coating that is applied thereto, and so on). Such an additional layer or layers can combine with the at least one ancillary layer of the multilayer optical film product to provide a neutral-density filter 40 (and thus to provide that the resulting assembly is a vision-protection filter lens 1). In specific embodiments of this general type, a multilayer optical film product may comprise a multilayer optical film along with one or more ancillary layers having properties such that, if multiple (e.g., two, three, or four) layers of multilayer optical film product are stacked (e.g., laminated together), the ancillary layers form a neutral-density filter 40 in combination, without the necessity of adding any other layers (excepting possibly e.g. a PSA to provide that the filter lens can be laminated to a pane of a personal-protection apparatus).

It has been mentioned that any layer of filter lens 1 may serve more than one purpose. In particular embodiments of this type, the final achievement of a neutral-density layer 40 may only occur when filter lens 1 is actually mounted in place on the pane of a personal-protection apparatus, e.g., in the case that a PSA used to perform the attachment, also provides incremental radiation-filtering properties needed to meet the requirements of ANSI Z87.1-2010.

A vision-protecting filter lens 1 may be made as desired by producing any multilayer organic film 20, producing e.g. an organic polymer layer or layers with additives and/or surface coatings sufficient to provide a neutral-density filter 40, and combining (e.g., adhesively bonding) these together to form filter lens 1. However, it may be convenient to start with any suitable commercially available product. Some commercial products, as available from a manufacturer, might take the form of a multilayer optical film, or might take the form of a neutral-density filter. However, other commercial products may take the form of a film (whether single-layer or multilayer) that, while not meeting the herein-disclosed properties of a neutral-density filter, may be combined with one or more other films to form a neutral-density filter. For example, some commercial products may take the form of a multilayer optical film product that includes a multilayer optical film along with one or more ancillary layers, which multilayer optical film product may be combined with at least one other film (noting that the at least one other film may itself be a multilayer optical film product that comprises one or more ancillary layers) to provide a neutral-density filter. In specific embodiments, two or more multilayer optical film products, each including at least one ancillary layer (that is not a part of the alternating-layer stack of the multilayer optical film itself), may be combined to form a filter lens, with the ancillary layers of the multilayer optical film products combining to form a neutral-density filter. In some embodiments of this type, no other layers besides the multilayer film products (and an optional PSA to facilitate bonding the filter lens to a pane), are included in the filter lens.

Figure 3:
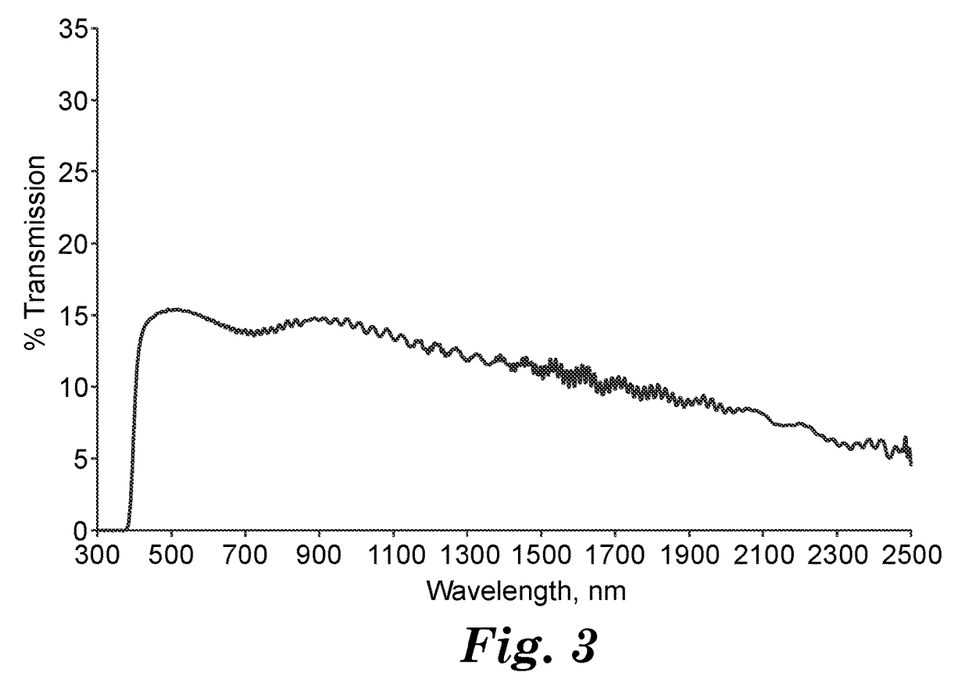
FIG. 3 contains transmission spectra for an exemplary neutral-density optical filter as disclosed herein.

A non-limiting list of commercial products that may be potentially useful in making a vision-protecting filter lens include products of the type available under the trade designation NIGHT VISION (e.g. NIGHT VISION 15, 25, or 35; FIGS. 3 and 4 present transmission data for the particular product designated NIGHT VISION 15); products available under the trade designation CM875 (FIG. 5 presents reflection data for this product); products available under the trade designation CM (COOL MIRROR) 330 (FIG. 6 presents reflection data for this product); products available under the trade designation CRYSTALLINE AUTOMOTIVE WINDOW FILMS (e.g., CR40, CR50, CR60, CR70, and CR90); products available under the trade designation BLACK CHROME AUTOMOTIVE WINDOW FILMS (e.g., BC10, BC20, BC35, and BC40); products available under the trade designation FX HP AUTOMOTIVE WINDOW FILMS (e.g., FX HP 5, FX HP 15, FX HP 20, FX HP 30, FX HP 35, and FX HP 50); and products available under the trade designation FX ST AUTOMOTIVE WINDOW FILMS (e.g., FX ST 5, FX ST 20, FX ST 35, FX HP 40, and FX ST 50. All of the above-listed products are available from 3M Company, St. Paul, Minn.

The determination of whether a purported filter lens includes a neutral-density filter as defined and described herein, can be done in any suitable manner. For example, if a purported filter lens is known to include a particular multilayer optical film, the percent transmission spectra of that multilayer optical film may be mathematically removed from the experimentally obtained percent transmission spectra for the purported filter lens. The spectra thus remaining, which can be considered to be the spectra exhibited by the remaining layers of the purported filter lens, can be evaluated to determine whether the remaining layers collectively qualify as a neutral-density filter. The ordinary artisan will appreciate that since a multilayer optical film as defined herein includes only the specific set of alternating layers of first (birefringent) polymer and second polymer, the optical spectra of such a multilayer optical film will be sufficiently well-behaved that it can be mathematically subtracted from the overall spectra contributed by the entire set of layers of the purported filter lens, in this manner If it is not known what particular multilayer optical film a purported filter lens includes, the transmission and reflection spectra of the purported filter lens may be used to infer the contribution of the multilayer optical film to the transmission spectra, which contribution may then be mathematically removed in the manner discussed above. Thus in at least some embodiments, if a purported filter lens displays a reflection spectra that shows that it includes a multilayer optical film as claimed herein, and if the transmission spectra of the purported filter lens meets the criteria disclosed herein for a neutral-density optical filter, it can be concluded that the purported filter lens does in fact include a neutral-density optical filter as claimed herein. In some circumstances it may be possible to physically separate the multilayer optical film from the other layers of the purported filter lens to perform a direct analysis of the purported neutral-density filter lens and/or of the multilayer optical film (noting while such operations may be performed for the purposes of characterization, a vision-protecting filter lens as claimed herein will not be separable in this manner, in ordinary operation and use of the filter lens).

The optical performance of a vision-protecting filter lens 1 (specifically, the attainment of relatively flat transmission of visible light, e.g. without preferentially passing green light while unduly blocking red light while), can be characterized by an a* measurement according to the well-known CIE 1976 (L*, a*, b*) color space characterization. The ordinary artisan will appreciate that a* values are often related on a nominal scale from −127 (at the green end of the scale) to +127 (at the red end). In various embodiments, a filter lens 1 as disclosed herein, will exhibit an a* value that is greater than at least about −50, −40, −30, −20, −10, or 0. In further embodiments, it will exhibit an a* value that is less than about +100, +80, +60, +40, or +10.

Filter lens 1 as disclosed herein may be used with any personal-protection apparatus, e.g. an apparatus worn as headgear or eyewear. A non-limiting list of such apparatus includes e.g. helmets, visors, faceshields (e.g. full and partial), goggles, respirators, and safety eyeglasses. (In this group, the term respirator is used in a functional sense to mean an apparatus that supplies filtered air to a user; it will be understood that respirators are available in many forms and embodiments, which may encompass many of the above-listed physical designs (e.g., helmets, faceshields, visors, and so on). In particular embodiments, the personal-protection apparatus is a powered air purifying respirator, as shown in exemplary embodiment in FIG. 8.

In some embodiments, vision-protecting filter lens 1 may be attached to a major surface of a visible-light-transmissive pane 102 of a personal-protection apparatus 100, as shown in exemplary embodiment in FIG. 8. It will be recognized that pane 102 will often be an eye-protecting pane, by which is meant an optically clear material whose primary purpose is to protect the user's eyes from particulate debris, splashing liquids, and so forth. An eye-protecting entity (e.g., pane) will be distinguished from a vision-protecting entity as disclosed herein, by which is meant an entity that protects the user from radiation, e.g. from high-intensity visible light. Pane 102 of personal-protection apparatus may comprise any suitable material that meets the standards appropriate for the particular person-protection apparatus. It is noted that the above discussions have primarily concerned assembling a filter lens 1 that will meet that optical requirements of ANSI Z87.1-2010. This standard may also require certain mechanical or physical properties; such properties will often be met by the personal protective equipment (including pane 102) with which filter lens 1 is used. It is further noted however that in some specific embodiments (e.g. in which vision-protecting filter lens 1 includes a rigid sheet as discussed below), filter lens 1 itself may e.g. supply, enhance, or augment such mechanical properties.

In some embodiments, pane 102 of personal-protection apparatus 100 may comprise at least one layer of transparent organic polymeric material, e.g. polycarbonate. In some embodiments, pane 102 may comprise at least one layer of transparent glass, e.g. borosilicate glass. In some embodiments, pane 102 may be a multilayer structure, e.g. laminated safety glass, wire-mesh safety glass, an organic polymeric layer with a scratch-resistant layer on a major surface thereof, and so on. The term pane is used in general and it is emphasized that the concept of attaching filter lens 1 to a pane 102 encompasses the attaching of filter lens 1 to any kind of outermost layer (e.g., a scratch-resistant layer, hardcoat layer, or the like) that may be present on any transparent sheet (of a personal protective apparatus) for which it is desired to provide or augment vision protection.

In some embodiments, filter lens 1 may be attached to a major outward surface of pane 102, in which position it may e.g. serve to protect pane 102 (particularly if pane 102 is an easily-scratched material, e.g. some polycarbonates). In other embodiments, filter lens 1 may be attached to a major inward surface of pane 102. In embodiments in which filter lens 1 exhibits asymmetric reflectivity, it may be convenient to position filter lens 1 so that the side that exhibits the highest reflectivity is facing outward.

In some embodiments, filter lens 1 may be adhesively attached (by which is meant attached by way of a pressure-sensitive adhesive, which concept will be well understood by the ordinary artisan) to a major surface of pane 102. In particular embodiments, filter lens 1 may be removably adhesively attached to pane 102 (e.g., by suitable choice of pressure-sensitive adhesive) so that a filter lens 1 may be e.g. removed and recycled/disposed, when desired. (In such a case, it may not matter whether filter lens 1 might be damaged in such removal, since its useful life may be over at this point.) Such removable adhesive attachment is contrasted with adhesive bonding that might be used in the assembling of filter lens 1 (e.g., in adhesively bonding a multilayer optical film 20 to a neutral-density filter module 40). In the latter case, the attachment/assembly is meant to be non-separable, so that filter lens 1, as made, is a unitary (e.g., sheet-like) structure that cannot be disassembled into its component parts in ordinary use of filter lens 1. If filter lens 1 is to be adhesively attached to pane 102, an optional pressure-sensitive adhesive may be present (as shown in exemplary embodiment as item 22 in FIG. 8) as filter lens 1 is supplied to a user. However, in other embodiments, a pressure-sensitive adhesive may be provided separately (e.g., as a separate sheet) that can be applied by the user to filter lens 1 (or to pane 102) to perform the adhesive bonding. Although adhesive bonding has been discussed above, any other method of bonding may be used, either instead of, or as an adjunct to, the adhesive bonding. Such methods may rely on one or more clips, clamps, and so on. In particular embodiments, an edge seal (that can be sealed to prevent radiation ingress, so that any radiation that reaches the users eye's can only do so by passing through filter lens 1) may be applied around the periphery of filter lens 1.

In some embodiments neutral-density filter 40 and multilayer optical film 20 may be made of relatively flexible layers so that vision-protecting filter lens 1 is compliant and conformable. In such embodiments, vision-protecting filter lens 1 can be conformed to (and e.g. adhesively attached to) a curved pane of a personal-protection apparatus. In some embodiments, filter lens 1 may be sufficiently conformable to be bent to a radius of curvature as small as about 4, 2, 1, or 0.5 cm (without unacceptably damaging any of the layers of filter lens 1). Any device that includes a rigid sheet, e.g. a rigid glass sheet, is not a conformable filter lens 1 according to this criteria.

In other embodiments, neutral-density filter 40 may include at least one rigid sheet (the term rigid is not meant to signify complete absence of bendability, but rather signifies a minimum bending stiffness on the order of that exhibited by a sheet of polycarbonate of thickness at least 1.0 mm). In some embodiments, such a sheet may exhibit a bending stiffness equivalent to that of a sheet of polycarbonate of thickness at least about 1.5, 2.0, 3.0, or 4.0 mm. The other layers of the neutral-density filter can be adhesively bonded to such a rigid sheet to form a filter lens pane. Thus, in embodiments of this general type, rather than vision-protecting filter lens 1 being attachable to an existing pane of a personal-protection apparatus, filter lens 1 may itself take the form of a filter lens pane that can be inserted (either permanently, or removably) into a window (e.g., an outward-facing through-hole) of a personal-protection apparatus. (In such cases, the rigid sheet to which the other layers are attached, is considered to be a part of the neutral-density filter.)

The discussions above have primarily concerned using filter lens 1 to provide passive vision protection in a personal-protection apparatus such as a respirator. For example, the approaches outlined above can allow a Shade Number of 3 to be imparted to the eye-protecting pane of a powered air purifying respirator. In embodiments of this type, a number of filter lenses may be packaged together (whether all of the same Shade Number, e.g. 3, or as an assortment of filter lenses of various Shade Numbers (e.g., 3, 4, 5 and/or 6)) to be selected from as desired by a user. Such filter lenses may thus be packaged as a kit e.g. along with instructions for use. In embodiments of this general type, filter lens 1 may be the primary, e.g. only, radiation-filtering apparatus of the personal protective equipment. Thus in such embodiments, filter lens 1 is not a component of, and is not used in association with, an autodarkening filter of any kind. However, in other embodiments filter lens 1 can serve as a passive vision-protection component to be used in combination with an autodarkening filter. The ordinary artisan will recognize that an autodarkening filter is an active device that can switch from a relatively light state to a relatively dark state in response to the detection of high intensity radiation (e.g., visible light). In some embodiments, filter lens 1 can provided in the optical path of an autodarkening filter e.g. to provide a constant, passive level of vision protection (e.g., at Shade Number of 3). The autodarkening filter can superimpose a darker shade level (e.g., to a Shade Number of e.g. 9, 11, or even higher) on the passive protection that is supplied by filter lens 1.

In embodiments in which filter lens 1 is used in combination with an autodarkening filter, components (layers) of the autodarkening filter will not be counted among the layers of filter lens 1 (specifically, the layers of neutral-density filter 40 of filter lens 1). In some embodiments involving an autodarkening filter, a filter lens 1 may be attached to the autodarkening filter (e.g., adhesively bonded to a major face thereof). In some embodiments, a filter lens 1 may be held against a major face (e.g., an outward face) of the autodarkening filter, e.g. by the pressure of a rigid cover sheet that sandwiches filter lens 1 between the rigid cover sheet and the autodarkening filter. In some embodiments, a frame may be used to hold such an assembly together to provide an autodarkening filter cartridge (e.g., of the general type described in U. S. Patent Application Publication 2014/0215673), e.g. with filter lens 1 incorporated into the cartridge. In some embodiments, a filter lens that is in the form of a filter lens pane may be a non-removable component of an autodarkening filter cartridge. In other embodiments, a filter lens pane might be fitted into a window of a personal protective apparatus, with an autodarkening filter being abutted against a major (e.g. inward) surface of the filter lens pane. In such embodiments, such a filter lens pane may thus serve as a removable/replaceable cover that provides physical protection for the automatic darkening filter as well as serving to provide passive vision protection.

List of Exemplary Embodiments

Embodiment 1 is a vision-protecting filter lens, comprising: a multilayer optical film that exhibits a left band edge in the range of from about 600 nm to about 900 nm, and, a neutral-density optical filter, wherein the vision-protecting filter lens exhibits a Shade Number of from 3 to 7.

Embodiment 2 is the vision-protecting filter lens of embodiment 1 wherein the vision-protecting filter lens is attached to a major surface of a visible-light-transmissive pane of a personal-protection apparatus chosen from the group consisting of goggles, helmets, faceshields, respirators, and safety eyeglasses. Embodiment 3 is the vision-protecting filter lens of embodiment 2 wherein the personal-protection apparatus is a powered-air purifying respirator and wherein the vision-protecting filter lens is attached to a major outward surface of the visible-light-transmissive pane of the powered-air purifying respirator. Embodiment 4 is the vision-protecting filter lens of any of embodiments 2-3 wherein the vision-protecting filter lens is removably adhesively attached to the major outward surface of the visible-light-transmissive pane by a pressure-sensitive adhesive. Embodiment 5 is the vision-protecting filter lens of embodiment 1 wherein the vision-protecting filter lens is a passive vision-protecting component that is present in the light path of an automatic darkening filter of a personal-protection apparatus.

Embodiment 6 is the vision-protecting filter lens of any of embodiments 1-5 wherein the vision-protecting filter lens exhibits a Shade Number of 3. Embodiment 7 is the vision-protecting filter lens of any of embodiments 1-5 wherein the vision-protecting filter lens exhibits a Shade Number of 5.

Embodiment 8 is the vision-protecting filter lens of any of embodiments 1-7 wherein a major surface of at least one layer of the neutral-density filter is attached to a major surface of the multilayer optical film. Embodiment 9 is the vision-protecting filter lens of embodiment 8 wherein a major surface of at least one layer of the neutral-density filter is adhesively attached to a major surface of the multilayer optical film. Embodiment 10 is the vision-protecting filter lens of embodiment 8 wherein the neutral-density filter is in the form of a module. Embodiment 11 is the vision-protecting filter lens of embodiment 10 wherein the neutral-density filter module is adhesively attached to a major surface of the multilayer optical film.

Embodiment 12 is the vision-protecting filter lens of any of embodiments 1-11 wherein the neutral-density optical filter exhibits a visible-light transmission slope with an absolute value that is no greater than about 6 percent transmission per 100 nm. Embodiment 13 is the vision-protecting filter lens of any of embodiments 1-11 wherein the neutral-density optical filter exhibits a visible-light transmission slope with an absolute value that is no greater than about 4 percent transmission per 100 nm. Embodiment 14 is the vision-protecting filter lens of any of embodiments 1-11 wherein the neutral-density optical filter exhibits a visible-light transmission slope with an absolute value that is no greater than about 2 percent transmission per 100 nm. Embodiment 15 is the vision-protecting filter lens of any of embodiments 1-11 wherein the neutral-density optical filter exhibits a visible-light transmission slope with an absolute value that is no greater than about 1 percent transmission per 100 nm.

Embodiment 16 is the vision-protecting filter lens of any of embodiments 1-15 wherein the neutral-density filter exhibits a percent transmission of less than 20 over the wavelength range of 300 nm to 1500 nm. Embodiment 17 is the vision-protecting filter lens of any of embodiments 1-16 wherein the multilayer optical film exhibits a left band edge in the range of from about 650 nm to about 850 nm. Embodiment 18 is the vision-protecting filter lens of any of embodiments 1-17 wherein the left band edge exhibits a slope of at least about 1 percent transmission per nm. Embodiment 19 is the vision-protecting filter lens of any of embodiments 1-17 wherein the left band edge exhibits a slope of at least about 2 percent transmission per nm. Embodiment 20 is the vision-protecting filter lens of any of embodiments 1-17 wherein the left band edge exhibits a slope of at least about 4 percent transmission per nm.

Embodiment 21 is the vision-protecting filter lens of any of embodiments 1-20 wherein the neutral-density filter comprises at least one layer chosen from the group consisting of a metal coating, a metal-oxide coating, and mixtures and combinations thereof. Embodiment 22 is the vision-protecting filter lens of any of embodiments 1-21 wherein the neutral-density filter comprises at least one layer chosen from the group consisting of aluminum, silver, antimony tin oxide, indium tin oxide, and mixtures and combinations thereof. Embodiment 23 is the vision-protecting filter lens of any of embodiments 1-22 wherein the neutral-density filter comprises at least one layer that is an organic polymeric material comprising an additive chosen from the group consisting of a dye, a pigment, and mixtures and combinations thereof. Embodiment 24 is the vision-protecting filter lens of any of embodiments 1-23 wherein the neutral-density filter comprises at least one layer that is an organic polymeric material comprising an additive chosen from the group consisting of calcium carbonate, titanium dioxide, carbon black, and mixtures and combinations thereof. Embodiment 25 is the vision-protecting filter lens of any of embodiments 1-24 wherein the neutral-density filter comprises at least one layer that is an organic polymeric material comprising a UV-blocker.

Embodiment 26 is the vision-protecting filter lens of any of embodiments 1-25 wherein the vision-protecting filter lens comprises a single multilayer optical film. Embodiment 27 is the vision-protecting filter lens of any of embodiments 1-25 wherein the vision-protecting filter lens comprises at least two multilayer optical films, with at least one layer that is not an optically active layer of a multilayer optical film being sandwiched between two multilayer optical films of the at least two multilayer optical films. Embodiment 28 is the vision-protecting filter lens of any of embodiments 1-27 wherein at least one layer of the neutral-density filter is separated from at least one other layer of the neutral-density filter, by at least one multilayer optical film. Embodiment 29 is the vision-protecting filter lens of any of embodiments 1-26 wherein no layers of the neutral-density filter are separated from any other layers of the neutral-density filter, by a multilayer optical film. Embodiment 30 is the vision-protecting filter lens of any of embodiments 1-29 wherein the multilayer optical film is comprised of alternating layers of polyester and poly(acrylic).

Embodiment 31 is a personal-protection apparatus comprising an eye-protecting pane, wherein the vision-protecting filter lens of any of embodiments 1-30 is attached to a major surface of the eye-protecting pane. Embodiment 32 is the personal-protection apparatus of embodiment 31 wherein the personal-protection apparatus is a powered air purifying respirator and wherein the vision-protecting filter lens is removably adhesively attached to an outward major surface of the eye-protecting pane of the powered air purifying respirator.

Embodiment 33 is a method of protecting the vision of a person, the method comprising: placing the vision-protecting filter lens of any of embodiments 1-30 into a light path between a light source and the eyes of the person, and, allowing visible and non-visible radiation from the light source to impinge on the vision-protecting filter lens and be filtered thereby. Embodiment 34 is the method of embodiment 32 wherein the light source is an artificial light source.

EXAMPLES

Procedures

Optical spectra (percent transmission, and percent reflection), may be obtained experimentally by using a spectrophotometer and integrating sphere, in generally similar manner as described in ASTM Test Method E903 as specified in 2012 (without performing solar weighting). Optical spectra for e.g. multilayer optical films may also be obtained by mathematical modeling techniques that are well known and understood by those of ordinary skill.

Representative Working Example

A multilayer optical film was obtained from 3M Company, St. Paul, Minn., under the trade designation CM330. A film product was obtained from 3M Company under the trade designation NIGHT VISION (NV) 15. Reflection data for the CM330 multilayer optical film is presented in FIG. 6 (it should be noted that this is modeled data; however, it corresponds closely with experimentally data that is available for this product.) Transmission data for the NV15 film product is presented in FIGS. 3 and 4. The two films were manually laminated together using the PSA that is a part of the NV15 product as supplied. Transmission data for the thus-formed filter lens (tested with the CM330 facing the radiation source) is presented in FIG. 7. The thus-formed filter lens was tested under ANSI Z87.1-2010 and was found to meet all optical requirements of the standard. The a* parameter was measured and was found to be approximately −8.8. (For comparison, two commercially available prior art Shade 3 lenses were tested and were found to respectively exhibit an a* parameter of approximately −29 and −59.) This revealed that the lens filter did not preferentially pass green light while unduly removing red light, which finding was in agreement with qualitative testing by human volunteers, who found that images viewed through the filter lens exhibited a relatively balanced spectral appearance (rather than e.g. the pronounced greenish tinge often found when using e.g. Shade Number 3 protective lenses of the art).

Samples of the above-described filter lens were laser cut to an appropriate shape to fit onto the curved pane of personal-protection apparatus (respirators) obtained from 3M Company under the trade designation VERSAFLO M-105 and M-305. The filter lens samples were laminated to the outward surface of the curved pane by way of a transfer tape obtained from 3M Company under the trade designation Y920XL. Human volunteers used these respiratory protection apparatus for test welding operations and reported that images viewed through the filter lenses exhibited a relatively balanced spectral appearance. It was also observed that the filter lenses served to protect the pane of the personal-protection apparatus, from being damaged by metal splatter that often occurs in welding operations.

Variation Working Examples

Various other exemplary filter lenses were produced by laminating together various commercially available film products. For example, a laminate of three layers of CR40, a laminate of two layers of CR40 plus one layer of CR50, and a laminate of two layers of CR40 plus one layer of CR60, were produced (all films were obtained from 3M Company, St. Paul, Minn.). These exemplary filter lenses were all found to meet the optical requirements of ANSI Z87.1-2010.

The foregoing Examples have been provided for clarity of understanding only, and no unnecessary limitations are to be understood therefrom. The tests and test results described in the Examples are intended to be illustrative rather than predictive, and variations in the testing procedure can be expected to yield different results. All quantitative values in the Examples are understood to be approximate in view of the commonly known tolerances involved in the procedures used.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). Although various theories and possible mechanisms may have been discussed herein, in no event will such discussions serve to limit the claimable subject matter. To the extent that there is any conflict or discrepancy between this specification as written and the disclosure in any document incorporated by reference herein, this specification as written will control.

What is claimed is:

1. A vision-protecting filter lens, comprising:
   a multilayer optical film that exhibits a left band edge in the range of from about 600 nm to about 900 nm, and,
   a neutral-density optical filter,
   wherein the vision-protecting filter lens exhibits a Shade Number of from 3 to 7.

2. The vision-protecting filter lens of claim 1 wherein the vision-protecting filter lens is attached to a major surface of a visible-light-transmissive pane of a personal-protection apparatus chosen from the group consisting of goggles, helmets, faceshields, respirators, and safety eyeglasses.

3. The vision-protecting filter lens of claim 1 wherein the vision-protecting filter lens is a passive vision-protecting component that is present in the light path of an automatic darkening filter of a personal-protection apparatus.

4. The vision-protecting filter lens of claim 1 wherein the vision-protecting filter lens exhibits a Shade Number of 3.

5. The vision-protecting filter lens of claim 1 wherein a major surface of at least one layer of the neutral-density filter is attached to a major surface of the multilayer optical film.

6. The vision-protecting filter lens of claim 5 wherein a major surface of at least one layer of the neutral-density filter is adhesively attached to a major surface of the multilayer optical film.

7. The vision-protecting filter lens of claim 5 wherein the neutral-density filter is in the form of a module.

8. The vision-protecting filter lens of claim 7 wherein the neutral-density filter module is adhesively attached to a major surface of the multilayer optical film.

9. The vision-protecting filter lens of claim 1 wherein the neutral-density optical filter exhibits a visible-light transmission slope with an absolute value that is no greater than about 4 percent transmission per 100 nm.

10. The vision-protecting filter lens of claim 1 wherein the neutral-density optical filter exhibits a visible-light transmission slope with an absolute value that is no greater than about 2 percent transmission per 100 nm.

11. The vision-protecting filter lens of claim 1 wherein the neutral-density filter exhibits a percent transmission of less than 20 over the wavelength range of 300 nm to 1500 nm.

12. The vision-protecting filter lens of claim 1 wherein the multilayer optical film exhibits a left band edge in the range of from about 650 nm to about 850 nm.

13. The vision-protecting filter lens of claim 1 wherein the left band edge exhibits a slope of at least about 1 percent transmission per nm.

14. The vision-protecting filter lens of claim 1 wherein the left band edge exhibits a slope of at least about 4 percent transmission per nm.

15. The vision-protecting filter lens of claim 1 wherein the neutral-density filter comprises at least one layer chosen from the group consisting of a metal coating, a metal-oxide coating, and mixtures and combinations thereof.

16. The vision-protecting filter lens of claim 1 wherein the neutral-density filter comprises at least one layer that is an organic polymeric material comprising an additive chosen from the group consisting of a dye, a pigment, and mixtures and combinations thereof.

17. The vision-protecting filter lens of claim 1 wherein the neutral-density filter comprises at least one layer that is an organic polymeric material comprising a UV-blocker.

18. The vision-protecting filter lens of claim 1 wherein the vision-protecting filter lens comprises a single multilayer optical film.

19. The vision-protecting filter lens of claim 1 wherein the vision-protecting filter lens comprises at least two multilayer optical films, with at least one layer that is not an optically active layer of a multilayer optical film being sandwiched between two multilayer optical films of the at least two multilayer optical films.

20. The vision-protecting filter lens of claim 1 wherein at least one layer of the neutral-density filter is separated from at least one other layer of the neutral-density filter, by at least one multilayer optical film.

21. The vision-protecting filter lens of claim 1 wherein no layers of the neutral-density filter are separated from any other layers of the neutral-density filter, by a multilayer optical film.

22. A personal-protection apparatus comprising an eye-protecting pane, wherein the vision-protecting filter lens of claim 1 is attached to a major surface of the eye-protecting pane.

23. The personal-protection apparatus of claim 22 wherein the personal-protection apparatus is a powered air purifying respirator and wherein the vision-protecting filter lens is removably adhesively attached to an outward major surface of the eye-protecting pane of the powered air purifying respirator.

24. A method of protecting the vision of a person, the method comprising:
   placing the vision-protecting filter lens of claim 1 into a light path between a light source and the eyes of the person,
   and,
   allowing visible and non-visible radiation from the light source to impinge on the vision-protecting filter lens and be filtered thereby.

25. The method of claim 24 wherein the light source is an artificial light source.

* * * * *